United States Patent [19]

Ogunro

[11] 4,445,234
[45] May 1, 1984

[54] PROSTHETIC NAIL FOR SURGICAL ATTACHMENT TO A FINGER OR TOE

[76] Inventor: E. Olayinka Ogunro, 625 Ray Ave., DeSoto, Tex. 75115

[21] Appl. No.: 399,477

[22] Filed: Jul. 19, 1982

[51] Int. Cl.³ .......................... A61F 1/00; A61F 1/24
[52] U.S. Cl. ............................................ 3/1; 128/77; 128/81 A; 132/73
[58] Field of Search ............................ 3/1; 132/73, 1; 128/81 R, 81 A, 77; D24/33; D28/56

[56] References Cited

U.S. PATENT DOCUMENTS

| 3,487,831 | 1/1970 | Jaume et al. ............... 128/81 R X |
| 3,765,410 | 10/1973 | Berens .......................... 128/81 A |

FOREIGN PATENT DOCUMENTS

| 1066777 | 10/1959 | Fed. Rep. of Germany ......... 132/73 |
| 1081913 | 6/1954 | France ................................ 3/1 |
| 662080 | 11/1951 | United Kingdom ................. 132/73 |
| 752960 | 7/1954 | United Kingdom ................... 3/1 |
| 821345 | 10/1959 | United Kingdom ................... 3/1 |

*Primary Examiner*—Ronald L. Frinks
*Attorney, Agent, or Firm*—Charles W. McHugh

[57] ABSTRACT

A prosthetic nail that is intended as a replacement or substitute for an injured or diseased nail for the digits on a hand or foot. Each embodiment of the invention generally consists of three main components: (1) a generally smooth and slightly curved plate having a rear edge that is adapted to be partially buried within the eponychial fold of a digit, somewhat like the proximal portion of a natural nail is buried; (2) an anchor member connected to the plate near the forward edge thereof and serving to anchor the forward part of the plate against unwanted movement with respect to the distal phalangeal bone; and (3) some means for preventing lateral movement of the plate with respect to the bone. Several versions of frontal anchor members are shown, and all versions share a characteristic of having at least some space into which the patient's tissue may be positioned for "mechanically" locking the prosthetic nail to the digit.

7 Claims, 8 Drawing Figures

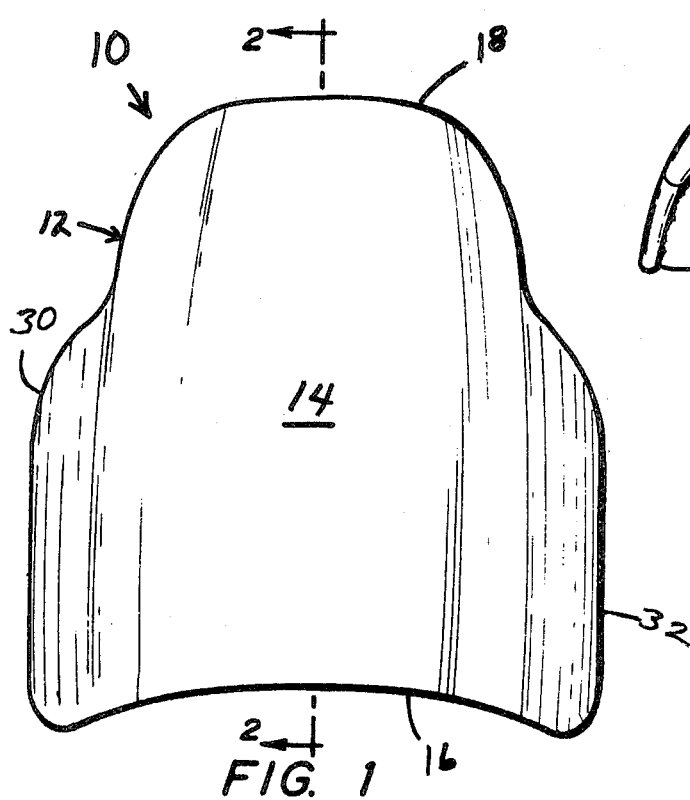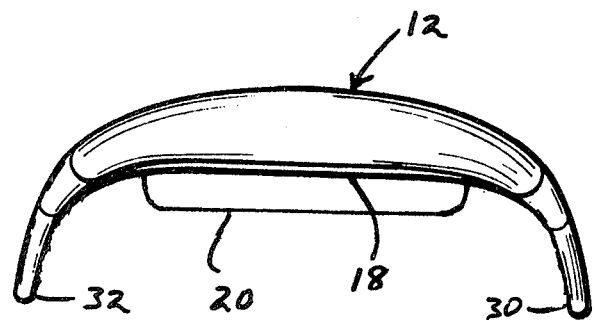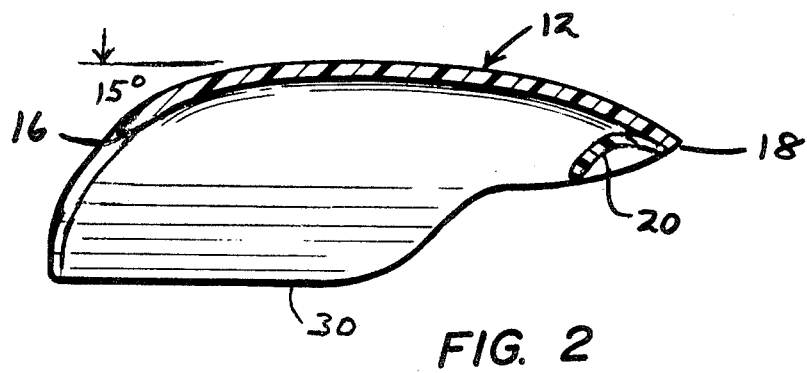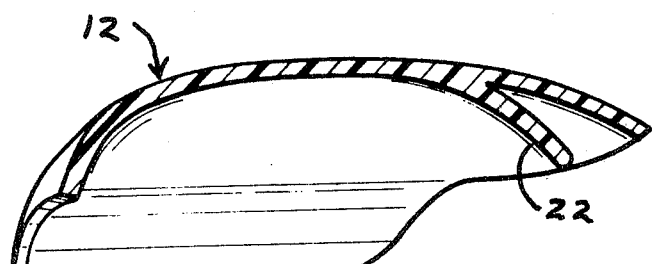

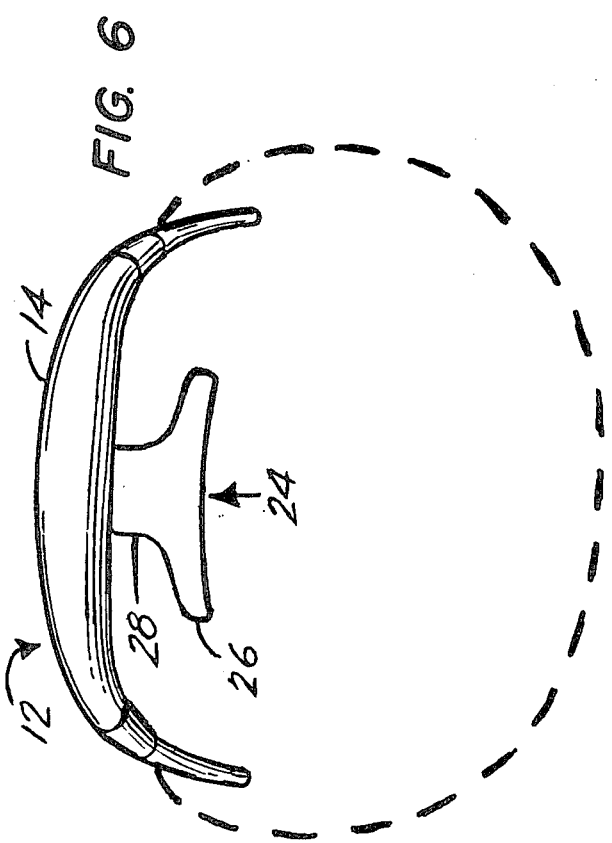
FIG. 5
FIG. 6
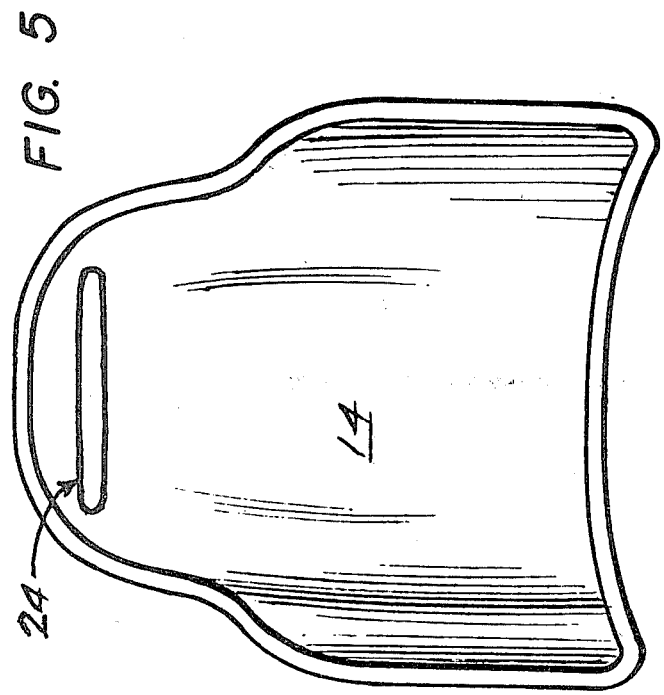
FIG. 7
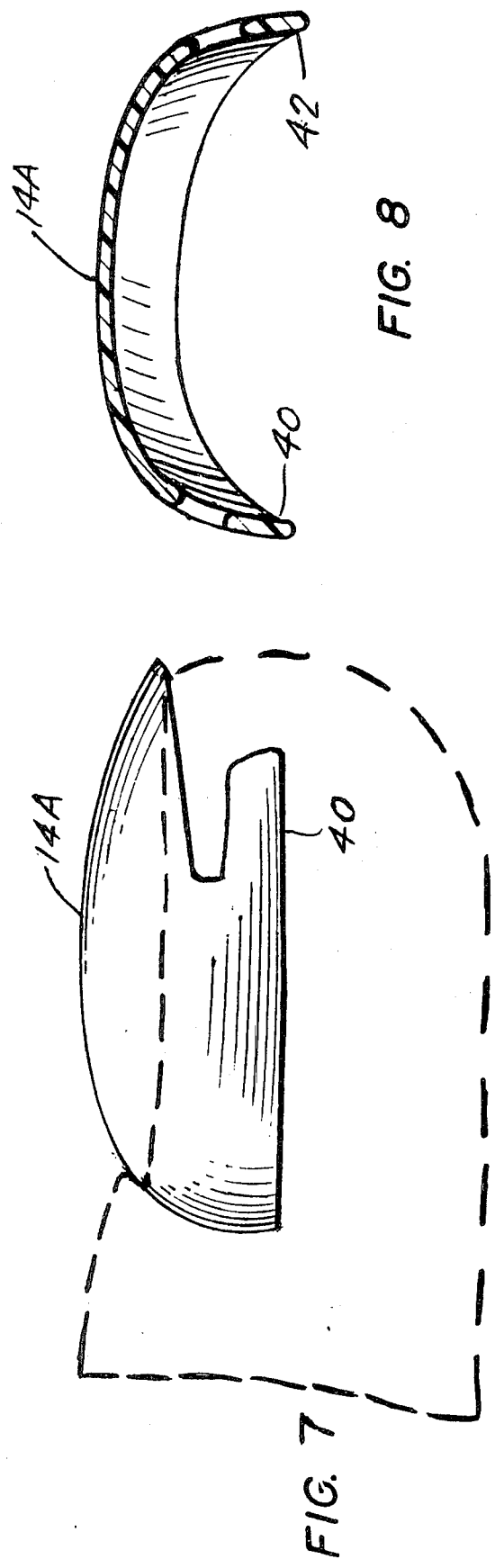
FIG. 8

PROSTHETIC NAIL FOR SURGICAL ATTACHMENT TO A FINGER OR TOE

CROSS-REFERENCE TO RELATED APPLICATION

This application discloses subject matter that is related to earlier-filed U.S. application Ser. No. 155,436 filed June 2, 1980 entitled "Prosthetic Nail", now U.S. Pat. No. 265,507.

BACKGROUND OF THE INVENTION

This invention relates generally to prosthetic nails for humans; more particularly, it relates to a prosthetic nail which is adapted to be surgically fitted to a finger or a toe so as to entirely replace a damaged or diseased nail.

It is well known that there are several million injuries to the fingertips that occur every year. This should not be surprising when one stops to think about how much humans depend on their hands in daily living, and how the hands are exposed to so many dangerous environments—including proximity to knives, hammers, drills, needles, farm implements, mallets, chisels, punches, grinders, air wrenches, shears, presses, clamps, saws, cutters, torches and other tools and machinery. In fact, it has been stated that from 30 to 40 percent of the annual industrial compensation payments to workers in the Unites States result from all types of injuries to the hand; and injuries to the fingertips constitute a large portion of those injuries.

In addition to debilitating injuries to the fingertips that are caused by accidents, there are also infections that can afflict the fingers in such a way as to render the nail functionally useless and/or so distorted as to even constitute an embarassment. There are fungi, for example, that can eventually convert a fingernail from a smooth, thin plate into a thick, irregular mass of hardened tissue bearing more resemblance to a massive scab than to a fingernail.

In addition to a person's fingers, the digits of a foot (i.e., the toes) are also vulnerable to many kinds of injuries. Lawn mowers in particular seem to contribute to many cutting injuries; and the dropping of heavy objects on the leading edge of a foot naturally contributes to many crushing injuries to the toes.

There has existed, therefore, a need for a prosthetic nail which can be used to replace in its entirety a natural nail that has become severely injured or diseased. This is not to say that there has never been any attempt to create an artificial nail for humans. In fact, there have been two reports in the journal "Plastic and Reconstructive Surgery" of previous efforts to create a fingernail of acrylic resin material that is glued to the nailbed of the finger. One of these reports describes work done by H. J. Buncke, Jr. and R. J. Gonzalez; the report is entitled "Fingernail Reconstruction" and it appears at Volume 30, pages 452–461 of "Plastic and Reconstructive Surgery" (1962). Another article entitled "Replacement of a Malformed Fingernail with Acrylic Resin Material" describes work by B. N. Bautista and S. B. Nery; it appears in the same journal at Volume 55, pages 234–236 (1975). Reference to other problems with fingers can be found in Chapter 32 of the book entitled "Plastic Surgery", 3rd Edition, edited by William C. Grubbs and James W. Smith, published by Little, Brown and Co. (1979). And, of course, there exists another form of what some might call "prior art", namely, the cosmetic nails that are sold in many stores for self-application (using an adhesive); these relatively cheap plastic nails are sold for the purpose of mending a broken nail or adding length to a short nail. Such cosmetic nails are merely glued on top of an existing fingernail or toenail in order to create what is described as a more pleasing appearance. Of course, such plastic appendages depend upon a natural nail for their connection to the finger or toe, and they have no structural features which would render them independently operable as prosthetic nails.

BRIEF DESCRIPTION OF THE DRAWINGS

FIG. 1 is a top plan view of one embodiment of a prosthetic nail;

FIG. 2 is a cross-sectional view of the prosthetic nail, taken in the plane represented by lines 2—2 in FIG. 1;

FIG. 3 is a front elevational view of the embodiment shown in FIGS. 1 and 2;

FIG. 4 is a cross-sectional view similar to FIG. 2 but showing an embodiment wherein an anchoring member extends forwardly with respect to the nail plate;

FIG. 5 is a bottom plan view of the alternate embodiment of the prosthetic nail, wherein an anchoring member extends downwardly at an angle of about 90° with respect to the general plane of the nail plate;

FIG. 6 is a front elevational view of the embodiment shown in FIG. 5, with the general outline of a person's finger being shown for general reference;

FIG. 7 is a side elevational view of another embodiment of the invention, superimposed upon a broken-line representation of a finger; and FIG. 8 is a front elevational view of the embodiment of the invention shown in FIG. 7.

BRIEF DESCRIPTION OF THE INVENTION

In brief, the invention includes a variety of embodiments of prosthetic nails that are intended for replacements or substitutes for injured or diseased nails. As used herein, the term "finger" shall be understood to refer broadly to all of the digits on a hand, including the thumb as well as what are commonly called the index, middle, ring and small fingers. And, the word "digits" shall be understood to refer generically to fingers and toes. Each embodiment of the invention generally consists of three main components: (1) a generally smooth and slightly curved plate having a rear edge that is adpated to be partially buried within the eponychial fold of a digit, somewhat like the proximal portion of a natural nail is buried; (2) a frontal anchor member that depends from the plate near the forward edge thereof and serves to anchor the plate against unwanted movement in a radial direction with respect to the distal phalangeal bone (which, for simplicity, will hereinafter be referred to simply as the "bone"); and (3) some means for preventing lateral movement of the plate with respect to the bone. Several versions of frontal anchor members are shown, and all versions share a characteristic of having at least some space into which the patient's flesh may be positioned for stabilizing purposes.

DETAILED DESCRIPTION OF THE INVENTION

Referring initially to FIG. 1, a prosthetic nail 10 in accordance with one embodiment of the invention includes a nail plate 12 which will typically have the proportions of a rectangle, with its length being about twice as long as its width. The nail plate 12 comprises a central and slightly curved sheet 14 having a proximal end 16 and a distal end 18; a longitudinal axis extends between the two ends 16, 18 in a direction parallel to the plane indicated by lines 2—2 in FIG. 1. The plate 12 is adapted to be mounted on top of the distal end of a digit (i.e., a finger or toe) so that the longitudinal axis of the plate extends in the same general direction as the distal phalangeal bone of the digit. Referring additionally to FIGS. 2 and 3, it will be seen that the sheet 14 is gently curved, both longitudinally and transversely, much like the bowl part of a spoon. As examined in a transverse plane, the sheet 14 is curved to the extent that it approaches the generally cylindrical cross-sectional shape of a typical digit.

The thickness of a preferred sheet 14 is slightly less than 1 millimeter, and the proximal end 16 has an edge that is sufficiently thin as to be at least partially buried within the eponychial fold of the digit. And, to foster this mating of the proximal end and the digit, the proximal end of the sheet forms an angle of about 15° (downwardly) with respect to the dorsal plane of the plate 12.

Referring specifically to FIGS. 2 and 3, an anchor member 20 extends downwardly from the distal end of the nail plate 12 for a distance which is adequate to create a significant space between the lower surface of the plate and a lower portion of the anchor member. It is this space into which some of a person's tissue is to be wedged or positioned so as to resist movement of the nail plate away from the distal phalangeal bone. In order to ensure that there will be sufficient tissue to serve this purpose, the "space" should have a depth in excess of 1 millimeter, and at least 2 millimeters of tissue space is preferred. The tissue may be surgically wedged or positioned between the anchor member 20 and the nail plate 12, or it may be established naturally by restorative growth of tissue into the space that is created by affixation of the nail 10. As shown in FIG. 2, the anchor member 20 constitutes a lip which extends downwardly from the distal end of the plate 12. Such a lip preferably makes an angle with respect to the plane of end 18 of at least 20° but not more than 70°; and said lip extends from the plate for a distance of at least 2 millimeters. An alternate embodiment of such an anchoring member is shown in FIG. 4, wherein lip 22 extends forwardly with respect to the nail plate 12, such that it protrudes in the same general direction as the distal end of the nail plate.

Referring next to FIGS. 5 and 6, anchor member 24 has a distal end 26 that is substantially wider than its proximal end 28; and tissue that completely envelopes anchor member 24 will tend to define a jug-like shape when viewed in cross section. That is, the envelope formed by the tissue will have a bulbous bottom that is connected to a narrow neck, corresponding to the narrow top of anchor member 24. Each of the illustrated anchor members may be either integrally formed with the nail plate 12 or joined thereto by ultrasonic welding or the like, depending upon the material that is selected for a particular embodiment and the configuration of an anchoring member that is chosen. A suitable material for the prosthetic nail is a medical grade silastic material which is moderately flexible (like a natural fingernail) but sufficiently firm as to resist destructive deformation. Other suitable materials include high density polyethylene and nylon. Perhaps it should be mentioned that the materials for a nail is selected only for its similarity in physical characteristics to natural nails and its compatability with human tissue on a long-term basis; the material need not be evaluated with regard to its compatability with any adhesives, because the prosthetic nail contemplated herein relies on what may be called a "mechanical" affixation technique—not one based on adhesives.

Additionally provided as a part of the prosthetic nail 10 is a means for providing lateral stability for the nail plate when it is installed on a digit. Such a means preferably includes at least one depending edge near the proximal end of a plate, which edge is adapted to be covered by tissue of the digit. As shown in FIG. 1, there are two depending elements which are connected to opposite sides of the sheet 14; the edges 30, 32 define the extreme limits of these two elements. These depending sides or skirts will typically rest alongside the distal phalangeal bone, and the depth of the side members as measured in a transverse plane will be within the range of about 2 to 4 millimeters such that they will be sufficiently covered by tissue as to preclude the nail 10 from being rotated about its anchor member 20. Of course, the longer the sides, the greater is the "anchoring" characteristic of those sides; but an important feature of a prosthetic nail is to provide a capability of picking up small things such as needles and the like. Hence, it is important to leave a forward edge of the nail that is not impeded by the presence of any side plates or skirts, etc.

In the event that the proximity of the prosthetic nail to the distal phalangeal bone is such as to make contact between them very likely as a result of only modest pressure on the nail, an anchoring technique as shown in FIGS. 7 and 8 may be utilized. In this construction, anchor members 40, 42 extend forwardly from the side plates for a distance which is sufficient to create the necessary space for anchoring tissue—but not so far as to go beyond the distal end of sheet 14A. While these side anchors 40, 42 are definitely advantageous when the nail bed of the digit is very thin or has been partially removed by an injury, they do lack the protection against the accidental insertion of a thin object under a prosthetic nail. For example, if a person sticks his hand into a pocket and an object like a fingernail file is resting "point up" in the pocket, the structural lip shown in FIG. 4 would obviously stop the object from being pushed under the nail plate, while no such protection is inherent in the embodiment shown in FIGS. 7 and 8. Nevertheless, the embodiment of FIGS. 7 and 8 may be almost compulsory in some circumstances, if a patient is to have the benefit of any kind of a prosthetic nail.

While only the preferred embodiments of the invention have been disclosed in detail herein, it should be apparent to those skilled in the art that modifications thereof can be made without departing from the spirit of the invention. Thus, any specific structure shown herein is intended to be exemplary and is not meant to be limiting, except as described in the claims appended hereto.

What is claimed is:

1. A prosthetic nail adapted for use on one of the digits of a person's hand or foot, comprising the combination of:
(a) a nail plate comprising a slightly curved sheet having proximal and distal ends and a longitudinal axis extending therebetween, and the plate being adapted to be placed on top of the distal end of a digit so that the longitudinal axis extends in the same general direction as the distal philangeal bone of the digit, and said plate being slightly curved as viewed in a transverse plane so as to approach the generally cylindrical cross-sectional shape of a typical digit, and said plate having a thin edge at its proximal end that is adapted to be at least partially buried within the eponychial fold of the digit;

(b) an anchor member extending downwardly from the distal end of the nail plate, and there being a space in excess of 1 mm between the lower surface of said plate and a lower portion of the anchor member, whereby, at least some tissue of a person's digit may be wedged between a lower portion of the anchor member and the nail plate, and whereby the wedged tissue can resist the movement of the nail plate away from the distal phalangeal bone; and (c) means for providing lateral stability for the nail plate when it is mounted on a digit, and said means including at least one depending edge near its proximal end that is adapted to be covered by tissue of the digit.

2. The prosthetic nail as claimed in claim 1 wherein the anchor member constitutes a lip which makes an angle of more than 20° and less than 70° with respect to the plate, and said lip extends from the plate for a distance of at least 2 mm.

3. The prosthetic nail as claimed in claim 2 wherein the lip extends forwardly with respect to the nail plate, so that the lip protrudes in the same general direction as the distal end of the nail plate.

4. The prosthetic nail as claimed in claim 2 wherein the lip extends rearwardly with respect to the nail plate, so that the lip protrudes toward the proximal end of the nail plate.

5. The prosthetic nail as claimed in claim 1 wherein said anchor member has a distal end that is substantially wider than its proximal end, whereby tissue that completely envelopes the anchor member may be described as defining a jug-like shape when viewed in cross section.

6. The prosthetic nail as claimed in claim 1 wherein said means for providing lateral stability for the proximal end of the nail plate constitutes a pair of side members which depend from respective sides of the sheet, and said side members each having a length less than the length of the curved sheet.

7. A prosthetic nail adapted for use on one of the digits of a person's hand or foot, comprising the combination of:

(a) a nail plate comprising a slightly curved sheet having proximal and distal ends, and the plate being adapted to be placed on top of the distal end of a digit so that it extends in the same general directions as the distal phalangeal bone of the digit, and said plate having a thin edge at its proximal end that is adapted to be at least partially buried within the eponychial fold of the digit;

(b) means for providing lateral stability for the nail plate when it is mounted on a digit, and said means including a pair of side members attached respectively to the two sides of the sheet, and the depth of the side members as measured in a transverse plane being within the range of about 2 to 4 millimeters, such that said side members are adapted to be at least partially covered by tissue of the digit; and (c) an anchor member extending forwardly from the leading edge of each side member, and there being a space in excess of 1 millimeter wide between the distal end of said plate and each of the anchor members, whereby at least some tissue of a person's digit may be positioned between an anchor member and the distal end of the nail plate, and whereby the tissue surrounding the anchor members can resist the movement of the nail plate away from the distal phalangeal bone.

* * * * *